United States Patent [19]
Colpaert et al.

[11] Patent Number: 5,948,806
[45] Date of Patent: Sep. 7, 1999

[54] TREATMENT OF PARKINSON'S DISEASE WITH (+)2-(ETHYL-2,3-DIHYDROBENZOFURANYL)-2-IMIDAZOLINE (DEXEFAROXAN OR (+) EFAROXAN)

[75] Inventors: Francis Colpaert, Castres; Michael Briley, Gaillac; Thierry Imbert, Viviers-les-Montagnes, all of France

[73] Assignee: Pierre Fabre Medicament, Boulogne, France

[21] Appl. No.: 08/825,414

[22] Filed: Mar. 26, 1997

Related U.S. Application Data

[63] Continuation of application No. 08/564,251, filed as application No. PCT/FR94/00715, Jun. 15, 1994, abandoned.

[30] Foreign Application Priority Data

Jun. 18, 1993 [FR] France ................................ 93 07379

[51] Int. Cl.⁶ .............................................. A61K 31/415
[52] U.S. Cl. ............................................................ 514/397
[58] Field of Search ............................................. 514/397

[56] References Cited

U.S. PATENT DOCUMENTS

| | | | |
|---|---|---|---|
| 5,173,502 | 12/1992 | Malen et al. | 514/396 |
| 5,281,607 | 1/1994 | Stone et al. | 514/280 |

FOREIGN PATENT DOCUMENTS

| | | |
|---|---|---|
| 0 071 368 | 2/1983 | European Pat. Off. . |
| 0 486 385 | 5/1992 | European Pat. Off. . |

OTHER PUBLICATIONS

Joly et al., Arch. Int. Pharmacodyn. Ther. 277(2) pp. 180–191, 1985.
Chapleo et al., J. Med. Chem. 27(5), pp. 570–576, 1984.
Ghika et al., Neurology 41(7), pp. 986–991, 1991.
Mavridis et al., Brain Res. 562(2) pp. 216–224, 1991.
Craig et al. "Modern Pharmacology", p. 16, 1982.
Christopher Chapleo, et al., α–*Adrenoreceptor Reagents. 2. Effects of Modification of the 1,4–Benzodioxan Ring System on α–Adrenoreceptor Activity*, J. Med. Chem. 27, 570–576 (1984).
Michael Stillings, Christopher Chapleo, et al., α–*Adrenoreceptor Reagents. 3. Synthesis of Some 2–Substituted 1,4–Benzodioxans as Selective Presynaptic $α_2$–Adrenoreceptor Antagonists*, J. Med. Chem. 28, 1054–1062 (1985).
Costall B. and Naylor R.J. *A comparison of circling models for the detection of antiparkinson activity.* Psychopharmacologia 41, 57–64, 1975.
Silverman P.B. *On–off effects of dopamine receptor agonists in the hemi–parkinsonian rat.* Eur. J. Pharmacol. 242, 31–36, 1993.
Ungerstedt U. *Post–synaptic supersensitivity after 6–hydroxy–dopamine induced degeneration of the nigrostriatal dopamine system.* Acta Physiol. Scand. 367, 69–93, 1971.

*Primary Examiner*—Raymond Henley, III
*Attorney, Agent, or Firm*—The Firm of Gordon W. Hueschen

[57] ABSTRACT

The present invention relates to the use of efaroxan and its derivatives for the preparation of a medicinal product intended for the treatment of Parkinson's disease.

1 Claim, No Drawings

TREATMENT OF PARKINSON'S DISEASE WITH (+)2-(ETHYL-2,3-DIHYDROBENZOFURANYL)-2-IMIDAZOLINE (DEXEFAROXAN OR (+) EFAROXAN)

The present application is a file wrapper continuation of application Ser. No. 08/564,251, filed Dec. 15, 1995, now abandoned, which is a 371 of PCT/FR94/00715 filed Jun. 15, 1994.

The present invention relates to the use of efaroxan and its derivatives for the preparation of a medicinal product intended for the treatment of Parkinson's disease.

Parkinson's disease is a neurodegenerative disease especially affecting the neurons of the substantia nigra—pars compacta—and its nigrostriatal projections. The symptomatic manifestations are motor disorders such as tremor, muscular rigidity and hypokinesia. Diagnosis of the disease is exacting, only a histological analysis performed postmortem, by the demonstration of cell degeneration in the substantia nigra, enables the diagnosis to be asserted unambiguously. This degeneration gives rise to a dopaminergic deficiency which manifests itself in these three motor disorders. In the absence of histopathological evidence, the clinical features determine whether or not this disease is responsible for the observed manifestations.

At the present time, the treatment of Parkinson's disease is carried out, inter alia, by the use of doper-minergic substances, especially L-DOPA, where appropriate combined with an L-DOPA decarboxylase inhibitor such as carbidopa in order to avoid the peripheral side effects of L-DOPA on the cardiovascular system, and thus to optimize its central effects.

This therapy compensates for the excessively low endogenous cerebral levels of dopamine and improves the symptomatology of the disease without, however, treating its cause. It possesses major drawbacks such as tardive dyskinesia, and adverse effects of a gastrointestinal and cardiovascular nature. Furthermore, there is a fall-off of effect. L-DOPA does not stop the progression of the disease since the symptoms reappear immediately after the treatment is stopped. A need exists for therapy directed towards the recovery of neuronal degeneration.

Efaroxan, 2-(2-ethyl-2,3-dihydrobenzofuranyl)-2-imidazoline, is known to possess antagonist properties towards $\alpha_2$-adrenoceptors.

This compound is described in Patent GB-2,102,422 by its chemical structure in a general formula, its process of synthesis, its pharmaceutical formulations and its therapeutic application as an anti-depressant medicinal product and for the treatment of migraine.

This compound is also described in Patent WO 92/05,171, where the action of the laevorotatory enantiomer for treating diabetes, as a potassium channel-blocking agent, is demonstrated.

Various studies have also been carried out on monkeys or rats to evaluate the action of different compounds on symptoms analogous to those of Parkinson's disease, such as the "symptoms" induced by reserpine in rats (F. C. COLPAERT, Neuropharmacology, 26, 1431, 1987) or by the neurotoxin MPTP (F. C. COLPAERT et al., Brain Res. Bull., 26, 627, 1991), or alternatively the symptoms associated in man with another extrapyramidal disease: progressive supranuclear palsy (J. GHIKA et al., Neurologie, 41, 986, 1991).

The compounds studied were chosen from various dopamine agonists, anticholinergics, 5-HT agonists, histamine and some $\alpha$-adrenoceptor agonists or antagonists including idazoxan.

However, these general studies focused on induced diseases which, while possessing a number of similarities in respect of a few symptoms, are different, and, in particular, supranuclear palsy is distinguished therefrom by the fact that it affects only the intrinsic neurons of the neostriatum and that dopaminergic treatments (L-DOPA) do not induce improvements.

Now, it was found unexpectedly that the use of efaroxan or one of its derivatives not only enabled Parkinson's disease to be treated, but also made it possible to observe a persistence of the improvements obtained, even after the treatment was stopped.

The present invention hence relates to the use of efaroxan and its derivatives for the preparation of a medicinal product intended for the treatment of Parkinson's disease and of its progression.

Efaroxan and its derivatives are understood to mean the compound of formula I

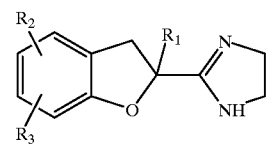

in which
$R_1$ represents a hydrogen atom or a linear or branched $C_1$-$C_6$ alkyl group,
$R_2$ represents a hydrogen atom or a methyl, chloro, bromo or fluoro group,
$R_3$ represents a hydrogen atom or a methyl, hydroxyl, methoxy, fluoro, chloro or bromo group,
in its racemic form and in the optically active form of its two enantiomers, as well as the therapeutically acceptable salts.

Preferably, $R_2$ and $R_3$ represent a hydrogen atom and $R_1$ represents an ethyl group or an n-propyl group.

PHARMACOLOGICAL STUDY

A pharmacological study was carried out in rats according to Ungerstedt's test (Acta Phys. Scand. (1971) 367, 67). The nigrostriatal dopaminergic projection was destroyed by injection of 6-OH-dopamine and pivoting was observed after administration of amphetamine. $\alpha_2$ receptor antagonists administered immediately before amphetamine increased pivoting in a dose-dependent manner (see Table 1). These results show a potentiation of the dopaminergic activity of amphetamine by stimulation of the noradrenergic pathway.

TABLE 1

| Product | Dose (mg/kp ip) | % effect |
|---|---|---|
| Methoxyidazoxan (RX 821002) | 0.16 | +94 |
|  | 0.63 | +83 |
| Efaroxan | 0.16 | +43 |
|  | 0.63 | +89 |

A microdialysis study was performed according to the conditions of Lategan et al., 1992 (A. J. LATEGAN, M. R. MARIEN, F. C. COLPAERT, Life Science 50, 995, 51992). A microdialysis probe was implanted in the striatum of the rat under anaesthesia. The dopamine level in the dialysate was analysed by HPLC. The administration of $\alpha_2$ receptor antagonists increased the dopamine level (see Table 2), suggesting an increase in dopamine release by stimulation of the dopaminergic pathway.

TABLE 2

| Product | Dose (mg/kp ip) | % effect on the DA level |
|---|---|---|
| Ethoxyidazoxan (RX 811059) | 10 | +200 |
| Efaroxan | 10 | +250 |

The increase in DA levels in the striatum together with behavioural tests induced by $\alpha_2$ antagonist substances result in the application of this property for obtaining medicinal products which are useful for treatment of Parkinson's disease.

PHARMACEUTICAL FORMULATION STUDY

The pharmaceutical compositions are administered orally in the form of hard gelatin capsules or of tablets containing 1 to 100 mg doses of active principle, and more especially 2.5 and 20 mg per capsule, or intravenously in the form of an injection containing a 0.1 to 10 mg dose of efaroxan.

CLINICAL STUDY

A pilot study was performed, and 20 patients satisfying the idiopathic criteria of Parkinson's disease were selected. Two groups were formed, group I treated with efaroxan and group II on placebo. The symptomatology was observed before treatment and at the end of one month of treatment (see Table 3). The dosage was 6 to 8 mg daily (and more when well tolerated).

TABLE 3

|  | Before treatment | After treatment |
|---|---|---|
| Group I | ++++ | ++ |
| Group II | ++++ | ++++ |

+ = severity of motor disorders.

These results show that the treatment of Parkinson's disease with an $\alpha_2$ antagonist such as efaroxan or its derivatives brings about an improvement in the symptomatology and is capable of having a favourable effect on the rate of progression of the disease.

We claim:

1. A method of treating Parkinson's disease and its progression comprising the step of administering to a patient suffering therefrom an effective dose of a compound selected from (+) efaroxan of formula I

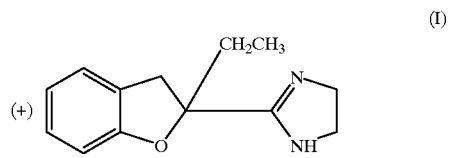

and its therapeutically-acceptable salts.

* * * * *